(12) United States Patent
Markoll

(10) Patent No.: US 7,588,529 B2
(45) Date of Patent: Sep. 15, 2009

(54) APPARATUS FOR TREATING A PATIENT'S BODY USING AN ELECTROMAGNETIC FIELD

(76) Inventor: Richard Markoll, Denninger Strasse 104, 81925 Munich (DE)

(*) Notice: Subject to any disclaimer, the term of this patent is extended or adjusted under 35 U.S.C. 154(b) by 101 days.

(21) Appl. No.: 11/053,665

(22) Filed: Feb. 9, 2005

(65) Prior Publication Data
US 2005/0203332 A1 Sep. 15, 2005

(30) Foreign Application Priority Data
Feb. 11, 2004 (EP) .................................. 04003008

(51) Int. Cl.
*A61N 1/00* (2006.01)
(52) U.S. Cl. ............................................. 600/13; 600/9
(58) Field of Classification Search ............... 600/9–15, 600/407, 410, 415, 421, 422; 378/121, 137
See application file for complete search history.

(56) References Cited

U.S. PATENT DOCUMENTS 5,131,904 A * 7/1992 Markoll ........................ 600/14

2001/0038683 A1 11/2001 Ritter et al.

FOREIGN PATENT DOCUMENTS

| EP | 0 048 451 A1 | 3/1982 |
| EP | 1 366 781 A1 | 12/2003 |
| EP | 1 371 388 A2 | 12/2003 |
| WO | WO 00/53259 | 9/2000 |

* cited by examiner

*Primary Examiner*—Charles A Marmor, II
*Assistant Examiner*—Christine D Hopkins
(74) *Attorney, Agent, or Firm*—The Nath Law Group; Jerald L. Meyer; Sungyeop Chung

(57) ABSTRACT

An apparatus for treating a patient, comprising a cylindrical coil (1) for generating an electromagnetic field, the cylindrical coil (1) being arranged so as to accommodate at least part of the patient's body and subject it to said electromagnetic field; means (3) for driving the coil (1) by a pulsed DC voltage; and a supporting structure (4) comprising a receiving surface (5) configured to support the body, or part of the body, inside said cylindrical coil (1); is characterized in that means (9) are provided to adjust the position of said coil (1) with respect to said receiving surface (5) in at least one direction.

16 Claims, 3 Drawing Sheets

APPARATUS FOR TREATING A PATIENT'S BODY USING AN ELECTROMAGNETIC FIELD

TECHNICAL FIELD

The present invention relates generally to an apparatus for treating the body of a patient using an electromagnetic field, and more particularly to an apparatus according to the preamble of claim 1.

An electromagnetic field can be applied to the body of a patient, or a part thereof, to alter, arrest, or heal diseases and conditions including painful, degenerative, injurious, or inflammatory conditions like, for example, osteoporosis and other musculoskeletal disorders, or to relieve pain or other uncomfortable or unwanted sensations associated with these named diseases and conditions.

RELATED BACKGROUND ART

It has been recognized in the prior art that the application of a magnetic field to diseased body parts can in some way improve the condition.

U.S. Pat. No. 5,131,904 discloses a process for treating an arthritic body organ, the process being performed in the absence of any electrical field and including the step of subjecting the arthritic body organ, to an electromagnetic field of under 20 Gauss and generated by an annular coil into the center of which the arthritic body organ is placed, the coil being driven by a pulsed DC voltage having a rectangular wave form consisting of an abruptly rising and abruptly deteriorating current pulsing at the rate of 1 to 30 pulse bursts per second. In this prior art apparatus, the target body part may be supported to be in position eccentric to the central flux portion of the magnetic field within the coil. This can be accomplished by a shapeable pillow which assists the proper positioning of the body part.

The therapy carried out by means of such an apparatus is now known as PST (pulsed signal therapy). Directing a specific time frequency and wave form, of low amplitude magnetic field into and onto a target body part in an almost axial arrangement for an extended specified length of time, allows or even causes the electron or ionic flow to remain in either a plus or minus state. This action does stimulate the electrical potential of the body part. Thus a regeneration process is initiated by which the cells are able to and will more fully perform their intended genetic functions.

In an apparatus developed by Dr. Markoll, the patient places the body part to be treated (in particular his arm, leg or torso) inside a cylindrical coil in which pulse signals are generated. The intensity and frequency of these pulsed signals are varied according to a predetermined biological pattern, depending on what kind of disease or condition is to be treated. The pulsed signals have a relatively low frequency and energy. To assist the proper positioning of the body part inside the coil, a shapeable pillow may be provided also with this apparatus.

SUMMARY OF THE INVENTION

It is an object of the present invention to provide an apparatus of the aforementioned kind, which is so constructed as to render the treatment of a patient's body more effective.

This object is solved by an apparatus according to claim 1. In said apparatus, means are provided to adjust the position of said coil with respect to said receiving surface in at least one direction.

By adjusting the position of the coil this way, the treatment becomes more effective. The reason for this is that using particular pulsed patterns, e.g. a pulsed pattern for treating osteoporosis, the electromagnetic field is stronger near the inner periphery of the coil than in the center of the coil. Therefore, the supporting structure according to the present invention is arranged so as to support the body part to be treated in a position where the electromagnetic field is relatively strong. Moreover, as a relative long wave length is used, the transverse components of the electromagnetic field, i.e. the components which are not parallel to the center axis of the coil, are substantially zero in this area of the coil.

Advantageous features of the present invention are disclosed in the dependent claims.

In a preferred embodiment, the coil is vertically movable with respect to the receiving surface, to allow the patient to have proximate contact with the treatment coil, irrespective of his or her physique. For more corpulent persons, the coil is raised; for slender persons, it is lowered. In this way, the coil offers an efficient contact relationship to the body. This adnexal contact relationship allows the delivery of a more effective treatment signal to the patient's body.

The raising and lowering of the coil can be realized by any suitable means, e.g. by means of a mechanical crank handle, pneumatically, hydraulically, or by an electric contrivance means.

In a preferred embodiment, the apparatus comprises a treatment bed on which the patient can rest during the treatment, the coil surrounding at least part of the length of said treatment bed.

The apparatus may then comprise a movable slide to allow the patient to be moved in the longitudinal direction of the bed into a treatment position within the coil.

In a preferred embodiment, the position (height) of the coil is indicated by a marking which displays the exact position of the coil, e.g. in relationship to the anterior aspect of the patient's upper body. Such an indicator can work mechanically or electrically, in particular digitally.

In case the coil is so arranged as to accommodate the entire body of the patient, the range for vertically displacing the coil is suitably within 0.1 to 50 cm, so that the coil can fit snugly about the body of the patient while also surrounding the lateral aspects of his or her body. The coil is preferably smoothly, steplessly adjustable, although a stepwise adjustment is, of course, also possible.

As regards the electromagnetic field used, preferably, its electromagnetic field strength is about 12.5 Gauss, and the pulsing rate is between 10 and 20 pulse bursts per second. It has been found out that these values are particularly suitable to be used in the inventive apparatus.

The pulsed DC voltage comprises time-varying rectangular pulses, at least some of which preferably have different durations and amplitudes. There might, however, sometimes be two or three adjacent pulses having the same duration and/or amplitude. As already pointed out above, the particular pulse pattern to be used in the apparatus according to the present invention depends on the disease or condition to be treated.

Preferably, said cylindrical coil has an inner diameter of about 58.05 cm (22 "). Such an inner diameter is suitable for treating the entire body of most patients.

In a particularly preferred embodiment of the invention, the ratio of duty cycle to off cycle of the pulses is more than 1. The off cycle is therefore always shorter than the duty cycle; the ratio might for example be 0.52 (duty cycle) to 0.48 (off cycle).

BRIEF DESCRIPTION OF THE DRAWINGS

Other features and advantages of the present invention will become readily apparent from the following description taken in conjunction with the accompanying drawings, in which.

DETAILED DESCRIPTION OF PREFERRED EMBODIMENTS

Preferred embodiments of the present invention will hereinafter be described with reference to the accompanying drawings.

Figure 1:
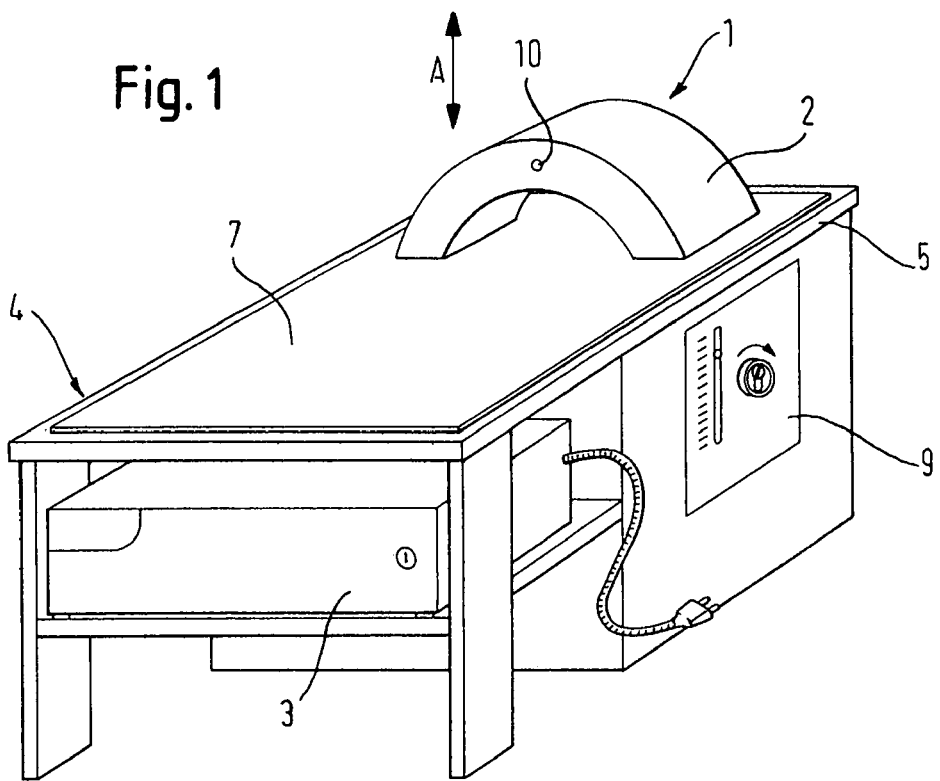
FIG. 1 shows an embodiment of an apparatus according to the present invention.

FIG. 1 shows a preferred embodiment of the apparatus according to the present invention in a perspective view.

The treatment bed shown serves for treating a patient's body. The apparatus comprises a cylindrical coil 1 disposed in a housing 2 which is made of plastic. The housing 2 has the shape of a ring, and its shape is adapted to the shape of the cylindrical coil 1. For energizing the coil using the above mentioned particular pulse patterns, a control unit 3 is provided, which is connected to the coil 1. A LED 10 is provided to indicate an active state of the apparatus.

In the embodiment shown, the coil has an inner diameter of about 60 cm; however, various internal diameters and lengths thereof are possible. The treatment coil 1 could as well extend over the full body length, in case it is desired to treat the entire body at once.

The apparatus further comprises supporting structure 4 having a rigid receiving surface 5 for supporting the patient's body (not shown) inside the coil 1.

The supporting structure 4 should be entirely made of a material which does not disturb the electromagnetic field. For example, the structure may be made of wood or plastics. On top of the receiving surface 5, a thin cushioning layer 7 may be provided which may be made of foam rubber.

According to the invention, the coil 1 and its housing 2 are vertically movable relative to the receiving surface 5 of the supporting structure 4 (in the direction of arrow A in FIG. 1), to allow the patient to have proximate contact with the treatment, coil, irrespective of his or her physique. For more corpulent persons, the coil 1 is raised; for slender persons, it is lowered. In this way, the coil 1 offers an efficient contact relationship to the body. This adnexal contact relationship allows the delivery of a more effective treatment signal to the patient's body.

Figure 3:
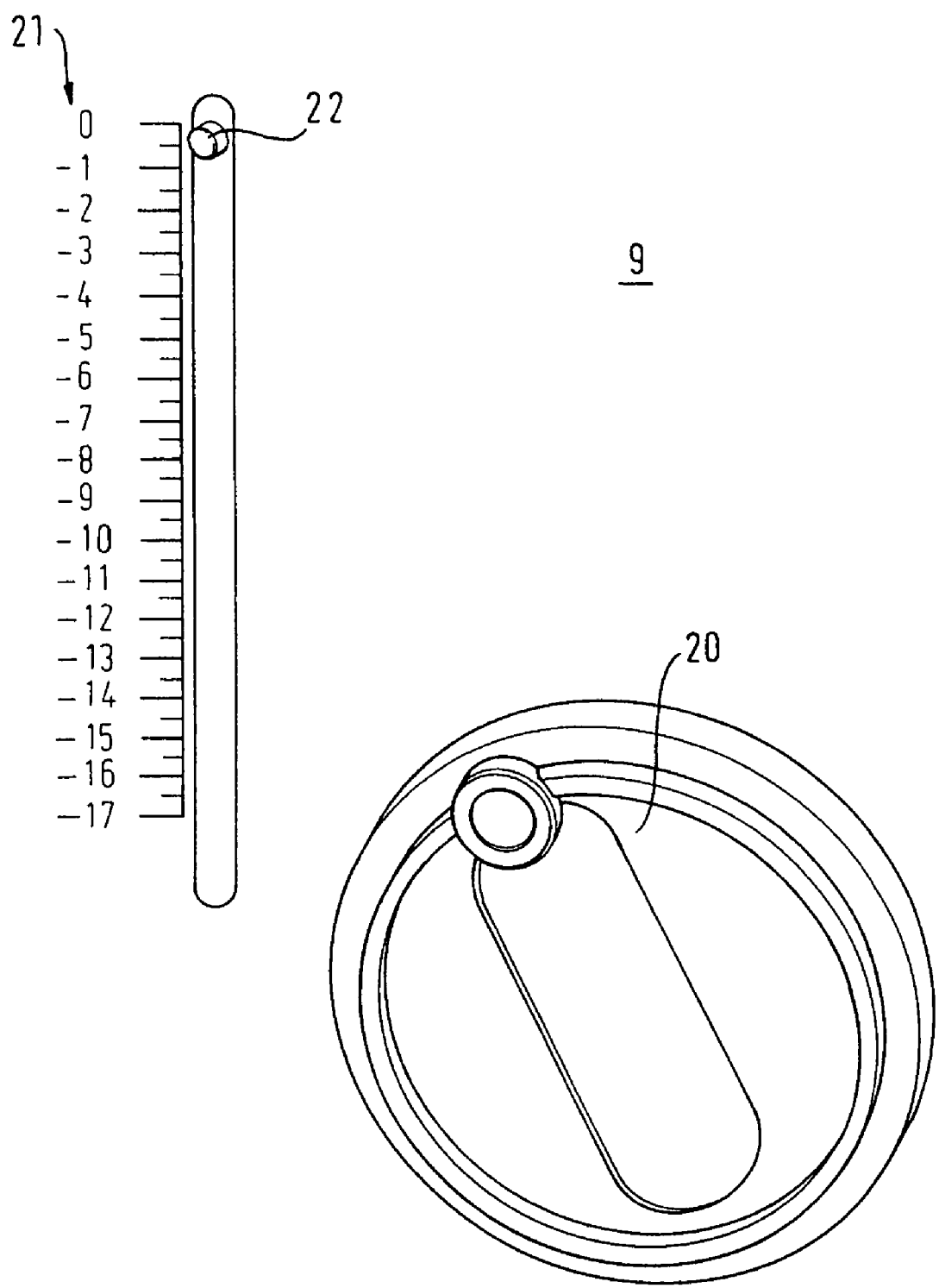
FIG. 3 shows in detail a calibration means of an apparatus according to the invention.

In the embodiment shown, the height of the coil 1 is adjustable by means of a calibration means 9. FIG. 3 shows said calibration means 9 in more detail: it comprises an adjustment wheel 20 as well as a mechanical indicator having a scale 21 and pin 22 which indicates the position of the coil 1 with respect to the receiving surface 5 of the supporting structure 4.

Figure 2:
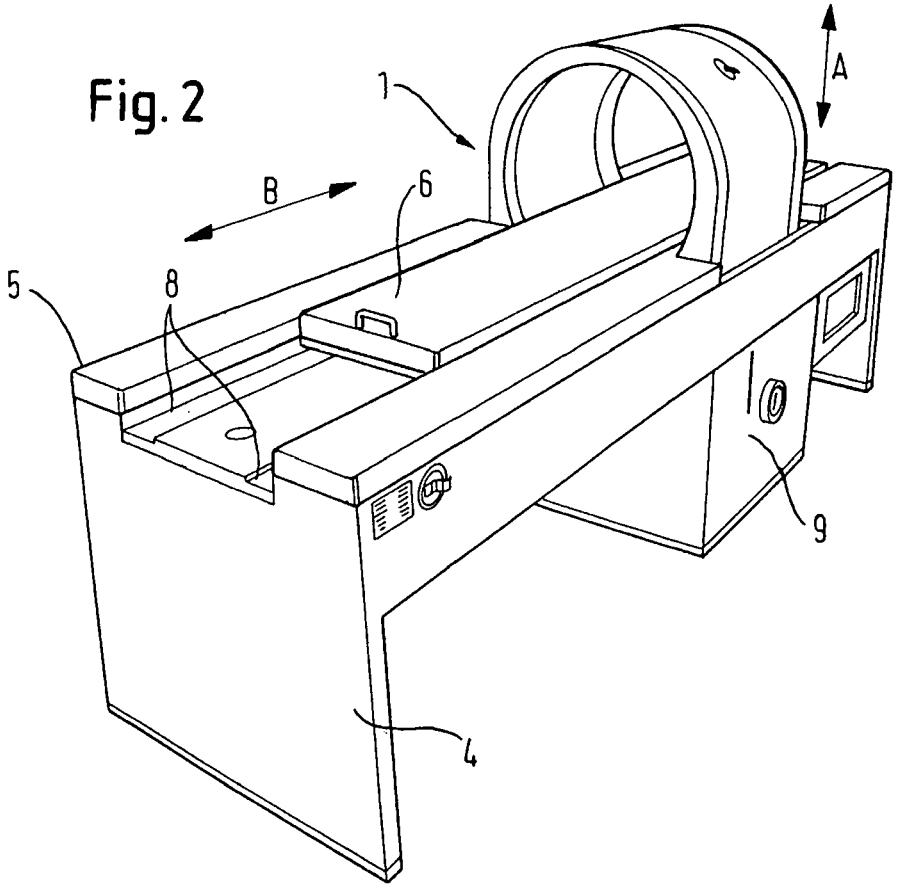
FIG. 2 shows another embodiment of an apparatus according to the present invention.

FIG. 2 shows another embodiment of the invention. This embodiment differs from the one in FIG. 1 in that a slide 6 is provided at the receiving surface of the supporting structure 4. By means of said slide 6, which is slidably supported by two rails 8, the patient can be conveniently slid into the coil 1 after having laid down onto the slide 6. That is, the patient rests in a prone position (i.e. flat on his or her back) on the slide 6 which is then pushed into and through the coil 1 on rails 8. The slide 6 can be moved by hand or operated by means of mechanical, pneumatic, hydraulic means or by electric contrivance means.

Also in the embodiment of FIG. 2, the coil 1 and its housing 2 are vertically adjustable with respect to the receiving surface 5 of the supporting structure 4. The position of the patient's body with respect to the coil 1 can, therefore, be adjusted both in the vertical direction (by adjusting the height of the coil 1 via the calibration means 9, arrow A) and in the horizontal direction (by moving the slide 6 within the coil 1, arrow B), so that the magnetic field can be exactly applied to a respective part of the body.

Figure 4:
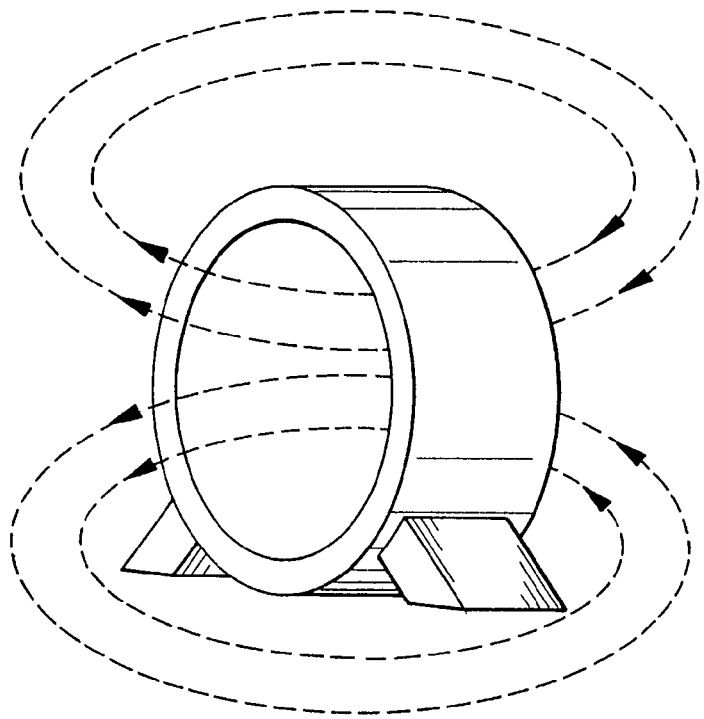
FIG. 4 shows schematically the shape of the electromagnetic field which is generated in the coil of the apparatus according to the present invention.

By energizing said cylindrical coil 1, an electromagnetic field is created. FIG. 4 schematically shows the shape of the generated field. It is an important characteristic of the invention that the field not be greater than 20 Gauss, preferably about 12.5 Gauss, in the area of the body part to be treated.

Figure 5:
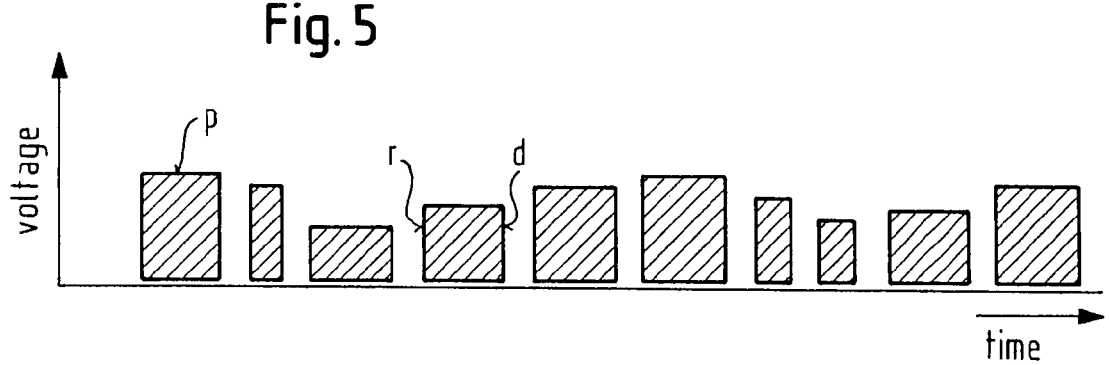
FIG. 5 shows a pattern of the voltage to be applied to the coil of the apparatus according to the present invention.

The voltage to be supplied to the coil C has a pattern as for example the one demonstrated in FIG. 5. The voltage supplied must repeatedly build up steeply, hold, and then deteriorate steeply and so that there are thus created a series of spaced working plateaus p of pure DC current. It is preferred, therefore, that in the duty cycle the wave form of the pure DC voltage involved be virtually of rectangular shape with the abruptly rising r and abruptly falling d sides of the wave form comprising sides of a rectangle. In between two such duty cycles there is an off cycle.

As pointed out above, the repetition rate of the pulses corresponds to a rate of 1 to 30 pulse bursts per second. For such a long wave length, the transverse components of the electromagnetic field, i.e. the components which are not parallel to the center axis of the coil, are substantially zero in this area of the coil.

It is moreover important that the movement of the field along the diseased body part be toward its distal end. This is achieved by supplying voltage of proper polarity to the coil leads.

Said pulsed DC voltage has a rectangular wave form consisting of abruptly rising and abruptly deteriorating current pulsing at the rate of 1 to 30, preferably 1 to 20 pulse bursts per second. At least some of the pulses have different durations and amplitudes.

In a particularly preferred embodiment of the invention, the ratio of duty cycle to off cycle of the pulses is more than 1. The off cycle is therefore always shorter than the duty cycle; the ratio might for example be 0.52 (duty cycle) to 0.48 (off cycle).

The present invention has been discussed so far by way of two embodiments, but should not be construed as being limited to the above embodiments, and it is taken for granted that the present invention may be properly changed and modified.

For example, in the above described embodiment, the coil is arranged in an upright position. The coil might, however, be as well arranged in a reclined position, for example for treating a patient's leg while he has put his foot on the floor. In this case, the supporting structure would serve as a kind of abutment for correctly positioning the body part relative to the coil.

Moreover, in the two above described embodiments, the coil 1 surrounds the body of the patient while he or she is resting on the receiving surface; the apparatus could, however, also be so constructed that the coil surrounds an arm or a leg to be treated. In this case, the dimensions of the coil are suitably adjusted.

What is claimed is:

1. An apparatus for treating a patient, comprising a cylindrical coil for generating an electromagnetic field, the cylindrical coil being arranged so as to accommodate at least part of a patient's body and subject it to said electromagnetic field; means for driving the coil by a pulsed DC voltage; and a supporting structure comprising a receiving surface configured to support the body, or part of the body, inside said cylindrical coil;

characterized in that means are provided to adjust a relative position of said coil with respect to a portion of said receiving surface surrounded by said coil in at least a vertical direction, wherein said cylindrical coil is disposed in a housing, the housing is either moved up or moved down vertically with respect to said receiving surface when the relative position of said coil is vertically adjusted by the means.

2. An apparatus according to claim 1, wherein the positioning of the coil with respect to the receiving surface is realized by means of a mechanical crank handle.

3. An apparatus according to claim 1, wherein said supporting structure comprises a treatment bed on which the patient can rest during the treatment, the coil surrounding at least part of the length of said treatment bed.

4. An apparatus according to claim 3, further comprising a movable slide slidably supported on the supporting structure by means of at least one rail, to allow the patient to be moved in the longitudinal direction of the supporting structure into a treatment position within the coil, and to exactly adjust said treatment position.

5. An apparatus according to claim 1, wherein said cylindrical coil has an inner diameter of about 58.05 cm.

6. An apparatus according to claim 1 wherein indication means are provided for indicating the position of the coil with respect to the receiving surface in at least one direction.

7. An apparatus according to claim 6, wherein said indication means is mechanically indicated.

8. The apparatus according to claim 6, wherein said indication means is electrically indicated.

9. The apparatus according to claim 8, wherein said indication means is digitally indicated.

10. An apparatus according to claim 1, wherein a range for vertically displacing the coil is within 0.1 to 50 cm.

11. An apparatus according to claim 1, wherein said coil is, in at least one direction, steplessly adjustable with respect to the receiving surface.

12. The apparatus according to claim 1, wherein the means for adjusting the vertical position of said coil are provided so as to support the body, or part of the body, to be treated in a position where the electromagnetic field is relatively strong.

13. The apparatus according to claim 12, wherein the position where the electromagnetic field is relatively strong is an eccentric position with respect to the central axis of said cylindrical coil.

14. An apparatus for treating a patient, comprising a cylindrical coil for generating an electromagnetic field, the cylindrical coil being arranged so as to accommodate at least part of a patient's body and subject it to said electromagnetic field; means for driving the coil by a pulsed DC voltage; and a supporting structure comprising a receiving surface configured to support the body, or part of the body, inside said cylindrical coil; characterized in that means are provided to adjust a relative position of said coil with respect to a portion of said receiving surface surrounded by said coil in at least a vertical direction, wherein the generated electromagnetic field contains pulses, a ratio of a duty cycle to off cycle of the pulses is more than 1, wherein said cylindrical coil is disposed in a housing, the housing is either moved up or moved down vertically with respect to said receiving surface when the relative position of said coil is vertically adjusted by the means.

15. The apparatus according to claim 14, wherein the means for adjusting the vertical position of said coil are provided so as to support the body, or part of the body, to be treated in a position where the electromagnetic field is relatively strong.

16. The apparatus according to claim 15, wherein the position where the electromagnetic field is relatively strong is an eccentric position with respect to the central axis of said cylindrical coil.

* * * * *